United States Patent [19]

Aboczky

[11] Patent Number: 5,061,270
[45] Date of Patent: Oct. 29, 1991

[54] SYSTEM FOR ORIENTING, INSERTING AND IMPACTING AN ACETABULAR CUP PROSTHESIS

[76] Inventor: Robert I. Aboczky, 323 E. Saddle River Rd., Upper Saddle River, N.J. 07458

[21] Appl. No.: 671,085

[22] Filed: Mar. 18, 1991

[51] Int. Cl.$^5$ ............................................... A61F 2/34
[52] U.S. Cl. .......................................... 606/91; 606/99
[58] Field of Search ................ 606/53, 86, 91, 99; 623/22, 23

[56] References Cited

U.S. PATENT DOCUMENTS

| | | | |
|---|---|---|---|
| 3,859,992 | 1/1975 | Amstutz | 606/91 |
| 4,305,394 | 12/1981 | Bertuch, Jr. | 606/91 |
| 4,632,111 | 12/1986 | Roche | 606/53 |
| 4,662,891 | 5/1987 | Noiles | 606/91 X |
| 4,987,904 | 1/1991 | Wilson | 606/53 X |
| 4,994,064 | 2/1991 | Aboczky | 606/91 |

Primary Examiner—Robert A. Hafer
Assistant Examiner—Sam Rimell
Attorney, Agent, or Firm—Anthony F. Cuoco

[57] ABSTRACT

A system for implanting an acetabular cup prosthesis includes an instrument and a disposable adapter. The disposable adapter engages the prosthesis and is supported on the instrument. The instrument is effective for orienting, inserting and impacting the prosthesis for implantation, after which the adapter is removed from the instrument for disposal. The adapter and the disposable prosthesis may be arranged as a pre-implantation assembly, thereby reducing the overall implantation time as is desirable.

10 Claims, 2 Drawing Sheets

SYSTEM FOR ORIENTING, INSERTING AND IMPACTING AN ACETABULAR CUP PROSTHESIS

BACKGROUND OF THE INVENTION

Total hip replacement procedures have been developed which include implanting an acetabular outer shell or cup prosthesis after appropriately preparing the acetabulum for the implantation. The actual implantation includes orienting, inserting and impacting the prosthesis in the acetabulum.

A variety of separate instruments have been required to accomplish the implantation. This has been found to be disadvantageous, particularly in view of the time and inconvenience required in switching from one instrument to another, which prolongs the overall operative time. In this connection it will be noted that a major problem encountered in performing surgical procedures such as herein referred to is the risk of infection of the operative area. This risk increases as the operative time increases, and hence it is most desirable to shorten the operative time to the greatest extent possible. Moreover, due to the nature of the procedure, it is imperative that it be performed under circumstances most auspicious to the patient and to the surgeon.

The invention disclosed in U.S. Pat. No. 4,994,064 issued on Feb. 19, 1991 to the present inventor overcomes the aforenoted disadvantages and simplifies the implantation, in that only one instrument is required for all of the segments of the procedure. With the instrument therein described an estimated fifteen to twenty minutes of operative time is saved, which is desirable for the reasons aforenoted.

The invention disclosed in U.S. Pat. Application Ser. No. 609,644 filed on Nov. 6, 1991 by the present inventor is an improvement over that disclosed in the referenced patent in that a locking arrangement is provided for the several operative members of the instrument thereby facilitating the use thereof, and a more versatile prosthesis alignment arrangement is provided to accommodate a variety of implantation situations as may from time to time occur.

The instruments disclosed in the aforementioned prior art require several operative members which co-act to grip the prosthesis so that said prosthesis can be oriented, inserted and impacted, after which the instruments are released from the gripped prosthesis. The present invention features a system for the purposes described including a simplified instrument and a disposable adapter for engaging the prosthesis removably retained thereby. The adapter engages the prosthesis in snap fit relation and the instrument removably supports an alignment arrangement whereby the system is effective for orienting, inserting and impacting the prosthesis in the acetabulum.

Accordingly, it is the object of the present invention to provide a system including an instrument and an adapter for orienting, inserting and impacting an acetabular cup prosthesis in a prepared acetabulum as part of a total hip replacement procedure, wherein a wide variety of implantation procedures can be accomplished with greater facility than has heretofore been the case.

SUMMARY OF THE INVENTION

This invention contemplates a system for orienting, inserting and impacting an acetabular cup prosthesis for implanting said prosthesis in the acetabulum. The system includes an instrument and a disposable adapter for the prosthesis. The instrument includes a cylinder and a spring biased rod displaceably supported therein, with one end of the rod extending beyond a corresponding end of the cylinder. The adapter is removably supported on the extending end of the rod. A ratchet member is supported by the cylinder near said corresponding end and is arranged to lock the adapter on the extending end of the rod and to unlock said adapter therefrom. The adapter is arranged to receive the prosthesis in snap fit relation and is thereafter locked via the ratchet on the extending end of the rod. The end of the cylinder opposite said corresponding end is arranged to receive an alignment arrangement for orienting the prosthesis to accommodate a variety of implantation procedures. The prosthesis so oriented is inserted into the acetabulum. Upon the prosthesis being so oriented and inserted, the instrument is impacted, whereby the prosthesis is seated in the acetabulum either by way of a press fit or by cementing, as the case may be. Upon the prosthesis being seated, the rod is displaced against the spring bias to push the adapter away from the seated prosthesis and the ratchet is actuated to unlock the adapter from the rod so that the adapter can be removed from the rod and disposed of, as is the intention of the invention. The instrument is thereupon removed from the prosthesis without disturbing its seating.

DETAILED DESCRIPTION OF THE INVENTION

Figure 1:
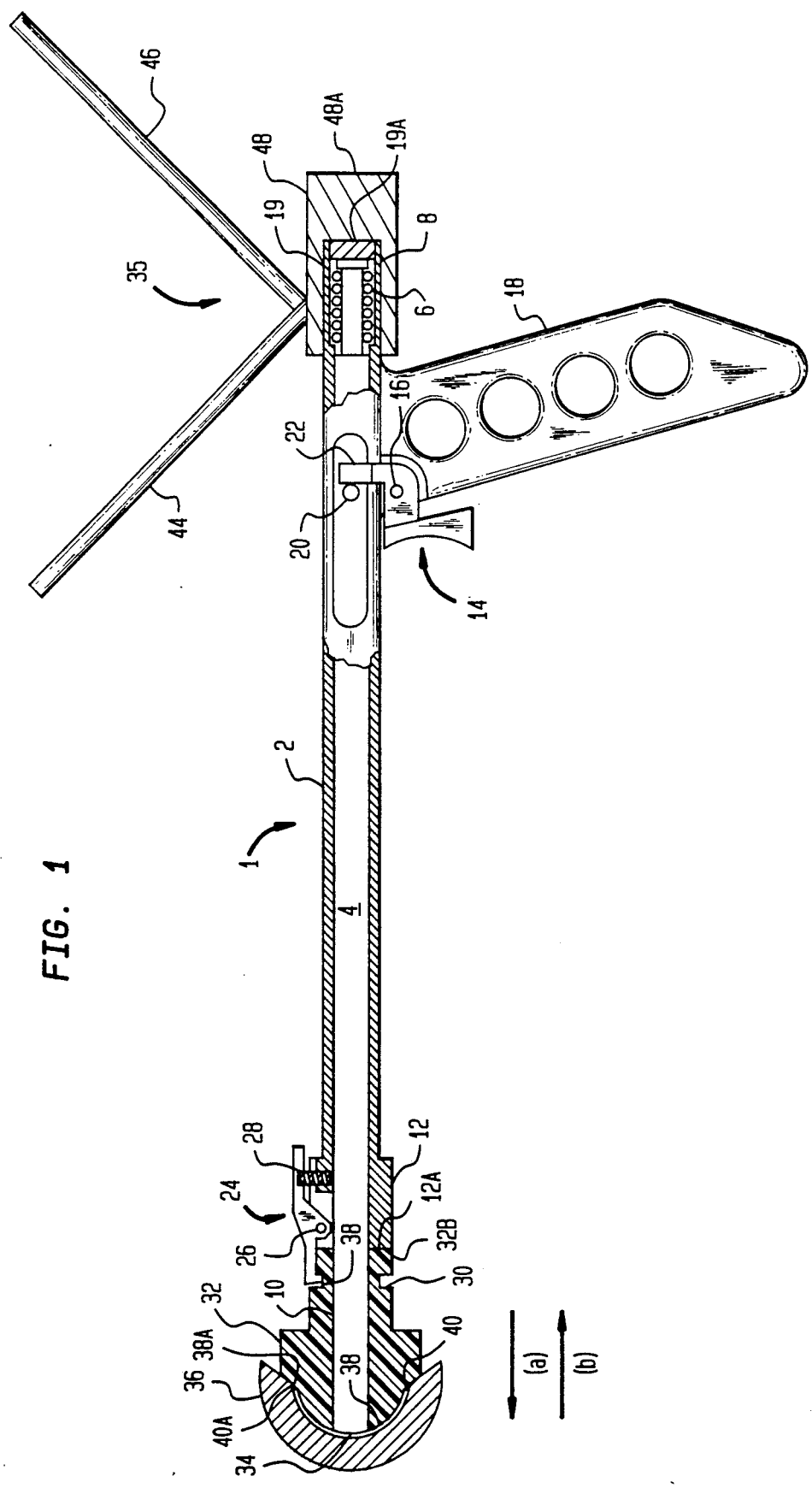
FIG. 1 is a diagrammatic, partially sectioned plan view representation showing a system according to the invention and arranged for orienting, inserting and impacting an acetabular cup prosthesis, and showing said prosthesis engaged thereby.

With particular reference to FIG. 1, the system of the invention includes an instrument designated by the numeral 1. Instrument 1 includes a cylinder 2. A rod 4 is disposed in sliding relationship within cylinder 2 and is biased by a spring 6 near one end 8 thereof. The opposite end 10 of rod 4 extends beyond a corresponding end 12 of cylinder 2.

A trigger arrangement 14 is pivotally mounted via a pivot pin 16 to a handle grip 18 which is integral with cylinder 2 near an end 19 opposite end 12 thereof and extends generally downwardly therefrom. Rod 4 carries a transversely extending pin 20 which abuts an actuating arm 22 of trigger 14. Thus, when trigger 14 is squeezed actuating arm 22 is effective via transversely extending pin 20 for displacing rod 4 out of cylinder 2 in the direction shown by arrow (a) in the figure. When trigger 14 is released, rod 4 retracts into cylinder 2 in the direction shown by arrow (b).

Cylinder 2 supports a ratchet arrangement 24 near end 12 thereof. Ratchet arrangement 24 is arranged via a pivot pin 26 and a biasing spring 28 to engage and disengage a circumferential slot 30 on an adapter 32. Adapter 32 is part of the system of the invention and is supported in sliding relationship on end 10 of rod 4.

End 19 of cylinder 4 is adapted to receive an alignment arrangement designated generally by the numeral 35. Alignment arrangement 35 fits over end 19 of cylinder 4 and is removably retained thereon as by a detent arrangement or the like (not otherwise shown). The purpose of alignment arrangement 34 will be hereinafter described.

With continued reference to FIG. 1, an acetabular cup prosthesis is designated by the numeral 36. The arrangement is such that adapter 32, which may be of a suitable plastic material or the like and supported on end 10 of rod 4 as aforenoted, is retained thereon when ratchet finger 38 biased by spring 28 engages slot 30. In this regard, it will be understood that, for purposes of alignment, cylinder 4 may include an alignment pin extending from face 12A thereof (not otherwise shown) which engages one of a plurality of equally spaced alignment holes (also not otherwise shown) in abutting face 32B of adapter 32.

Adapter 32 has a convex surface 38 and prosthesis 36 has a mating concave surface 40. The arrangement is such that adapter 32 accepts prosthesis 36 in snap fit relation. To this extent, convex surface 38 of adapter 32 may have a circumferentially extending rim or the like 38A and concave surface 40 of prosthesis 36 may have a mating circumferential surface 40A. Surfaces 38A and 40A are sized to achieve the desired snap fit arrangement.

Thus, with prosthesis 36 assembled to adapter 32 via the snap fit arrangement as heretofore noted, the resulting assembly is inserted on end 10 of rod 4 and appropriately aligned via the heretofore mentioned alignment pin on rod 4 and the alignment holes on adapter 32. Ratchet 24 is pressed against the bias of spring 28 and then released to engage slot 30, whereby the prosthesis/adapter assembly is locked to rod 4.

Figure 2:
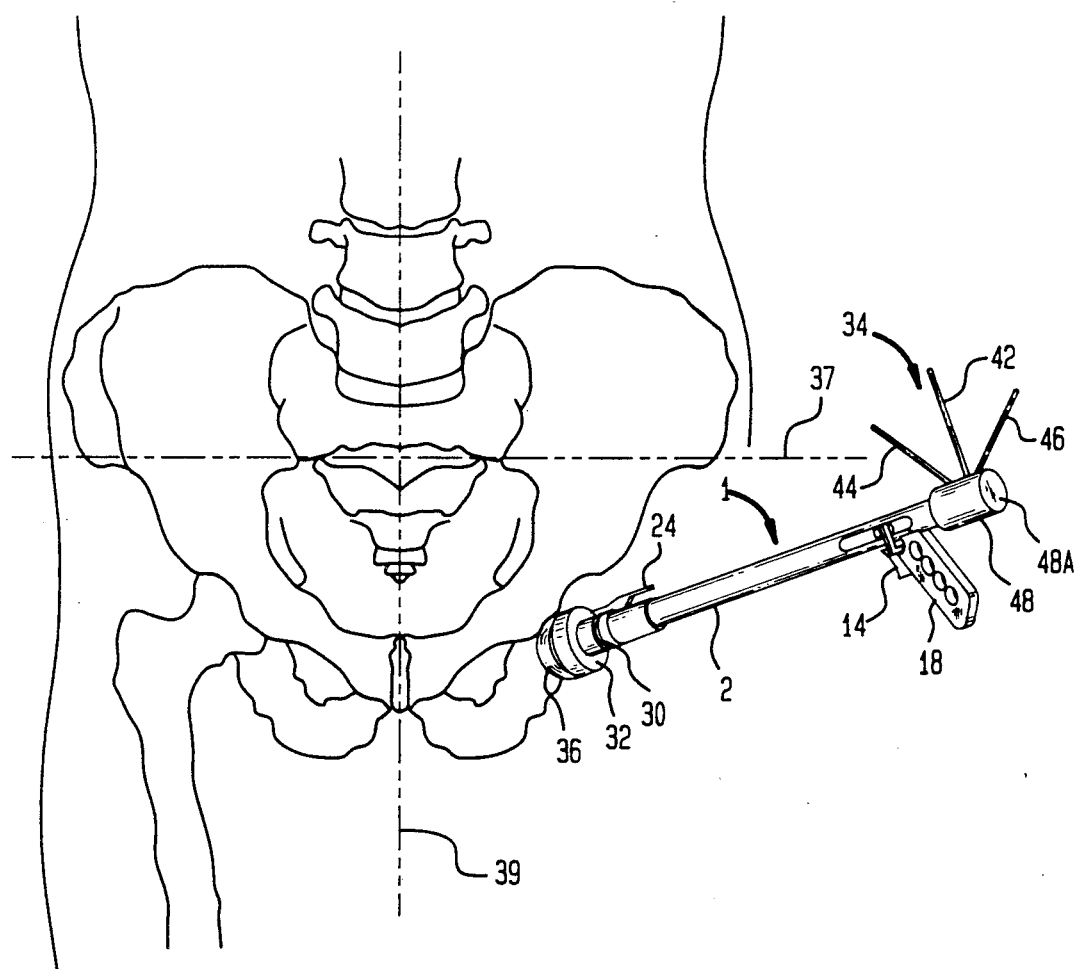
FIG. 2 is a diagrammatic representation showing a line between the right and left anterior/superior iliac spines, and which line is used for aligning the system of the invention.

With reference to FIGS. 1 and 2, alignment arrangement 35 is seen as including a pair of bars 42 and 44 and a bar 46. Bars 42 and 44 are fixedly spaced apart at an angle of approximately seventy-two degrees. Bars 42, 44 and 46 are supported on a cylinder 48 which is adjustably disposed on end 19 of cylinder 4 and fixed in an adjustable position by the aforementioned detent. In this regard, end 19 of cylinder 4 may have flats or the like provided thereon (not otherwise shown) which engage corresponding flats on the inside of cylinder 48 (also not otherwise shown) wherein cylinder 48 may be removably disposed in one of several positions on end 19 of cylinder 4, as will be understood by those skilled in the art.

USE OF THE INVENTION

In using the system described as aforenoted, i.e. with prosthesis 36 retained on adapter 32 and with adapter 32 supported and locked on end 10 of rod 4, bar 46 is disposed perpendicular to the plane in which the patient is supported, which is a substantially horizontal plane. With alignment arrangement 35 in a desired alignment position on cylinder 4, one of the alignment bars 42 or 44, depending on whether the prosthesis implantation procedure is being applied to the patient's right or left side, is aligned so as to be normal to line 37 (FIG. 2) which extends between the right and left anterior/superior iliac spines normal to the patient's pelvic line 39.

With instrument 1 thus aligned, which accomplishes the proper orientation of prosthesis 36, the prosthesis is inserted in the previously prepared acetabulum. End surface 48A of alignment arrangement cylinder 48 is impacted, whereby the prosthesis is seated in the acetabulum. Alternatively, alignment arrangement 35 may be removed from cylinder 2 and end surface 19A of end 19 of instrument cylinder 2 may be impacted to seat the prosthesis.

With prosthesis 36 so seated, trigger 14 is squeezed against the bias of spring 6 whereby rod 4 via pin 20 pushes against the prosthesis to release adapter 32 therefrom. The system of the invention including instrument 1 and adapter 32 is thereupon removed from the seated prosthesis.

Ratchet 24 is actuated against the bias of spring 28 so that finger 38 disengages slot 30, whereby adapter 32 is removed from end 10 of bar 4.

Since adapter 32 is intended to be disposable, it may be discarded, without further use of the particular adapter being contemplated. In this regard, it will be understood that it is a particular advantage of the present invention in that prosthesis 36 may be supplied to the surgeon together with adapter 32 engaged therein in snap fit relation. The engaged prosthesis and adapter may be packaged under sterile conditions and supplied to the surgeon just prior to the time that the actual implantation in performed.

It will be recognized that the system herein described has a versatility in use in that it may be used for an acetabular cup prosthesis which is either press fitted or cemented into the acetabulum. Significantly, the instrument saves a considerable amount of operative time, since it incorporates several different instruments as have heretofore been necessary and eliminates the time required in switching from one instrument to the other. Further, the time required in gripping an acetabular prosthesis as required in the earlier cited prior art is greatly reduced, since the prosthesis and the adapter may be pre-engaged and supplied to the surgeon as needed. Since the adapter is disposable, no particular arrangements need to be made for using the adapter for succeeding procedures as might otherwise be necessary.

The adapter can be fabricated of a suitable plastic material as aforenoted. The instrument itself can be fabricated from stainless steel, chrome steel or titanium so as to have a height and length and an overall weight acceptable for orthopaedic surgeons, and for meeting the demands of working within a relatively small cavity and having enough maneuvering space as is required.

The design of the instrument system is such that it retains the prosthesis in an ideal position, and holds it firmly so that even within the bony acetabulum, the prosthesis may be maneuvered to obtain ideal alignment. The instrument itself has the ability to withstand high temperatures necessary for sterilization processes prior to use. Further, its simplified design renders it easy to learn its usage and to receive wide acceptability by the orthopaedic community. The particular configuration wherein the adapter and the instrument combine to provide a prosthesis implantation system, and wherein the adapter may be engaged with the prosthesis prior to use and is disposable enhances the usage of the system.

The invention may be used with an acetabular prosthesis having an internal rim of any particular configuration. It will of course be understood that the engaging surface of the adapter is of the same configuration as is that of the prosthesis rim. Thus, it will be understood that the system of the invention may be adapted to any implantation arrangement wherein the acetabular prosthesis has an internal rim configuration which is circular, square, triangular, or any other shape, the same being within the scope of the invention. Likewise, the prosthesis may be of metal or may be of plastic, the same also being within the scope of the invention.

With the above description of the invention in mind, reference is made to the claims appended hereto for a definition of the scope of the invention.

What is claimed is:

1. A system for engaging an acetabular cup prosthesis and for orienting, inserting and impacting the prosthesis for implanting said prosthesis in the acetabulum of a patient, comprising:

an adapter for removably engaging the prosthesis in snap fit relation and having an external slot extending circumferentially therearound;

an instrument arranged for removably supporting the adapter removably engaged with the prosthesis, and operative for locking the supported adapter thereon, the instrument including an instrument cylinder, a rod disposed in sliding relation with the instrument cylinder and biased by a spring so that one end of the rod extends beyond a corresponding one end of the cylinder, the adapter supported on the extending end of the rod in sliding fit relation, and means supported near the one end of the instrument cylinder and operative for engaging the adapter slot to lock the adapter supported on the extending end of the rod on said rod;

the instrument further including means for orienting the prosthesis removably engaged with the adapter, whereupon the prosthesis is inserted in the acetabulum of the patient, and a surface which is impacted for seating the oriented and inserted prosthesis whereupon said prosthesis is implanted in the acetabulum;

said orienting means including an orienting cylinder in removable engagement with the end of the instrument cylinder opposite the one end thereof and adjustably positioned on said opposite end, the orienting cylinder supporting first, second and third alignment bars, with said first and second alignment bars being in a common plane and extending away from each other with a predetermined angle therebetween, the third alignment bar aligned perpendicular to a plane in which the patient is supported, and one of the first and second alignment bars, depending in which one of the right and left sides of the patient the prosthesis is being implanted, being aligned perpendicular to a line which extends between the patient's right and left anterior/superior iliac spines perpendicular to the patient's pelvic line, whereupon the prosthesis is oriented for implantation;

the instrument being operative for disengaging the adapter from the implanted prosthesis and for unlocking the adapter from the instrument, whereupon said adapter is removed from said instrument; and the impacted surface is a closed end surface of the orienting cylinder when said cylinder is in removable engagement with the opposite end of the instrument cylinder, and is a closed end surface of the opposite end of the instrument cylinder when the orienting cylinder in removable engagement with the instrument cylinder is removed therefrom.

2. A system as described by claim 1, including:

a head grip arranged with the instrument cylinder near the opposite end thereof;

trigger means mounted to the hand grip and having an actuating member;

the rod disposed in sliding relation within the instrument cylinder having a pin member extending transverse to the longitudinal axis of the rod and external the instrument cylinder for engaging the actuating member of the trigger means;

the trigger means being actuated, whereupon the actuating member pushes against the pin, with the rod thereupon being operative against the bias of the spring so that the extending end thereof pushes against the implanted prosthesis to break the snap fit relation between said prosthesis and the adapter;

the adapter supported and locked on the extending end of the rod being thereupon removed from the implanted prosthesis; and the means supported near the one end of the cylinder being operative for disengaging the slot to unlock the supported adapter so that said adapter can be removed from the instrument by sliding it off of the rod.

3. A system as described by claim 2, wherein:

the adapter removably engaging the prosthesis in snap fit relation is disposable;

said disposable adapter removably engaging the prosthesis in snap fit relation prior to said adapter being removably supported by the instrument; and the adapter being used for a single implantation, after which said adapter is disengaged from the implanted prosthesis and unlocked and removed from the instrument for disposal.

4. A method for implanting a prosthesis in the acetabulum of a patient, comprising:

removably engaging the prosthesis on an adapter;

removably supporting the adapter on an instrument and locking the adapter thereon;

orienting the prosthesis, including providing first and second alignment bars in a common plane and extending away from each other with a predetermined angle therebetween, providing a third alignment bar and aligning said third bar perpendicular to a plane in which the patient is supported, and aligning one of the first and second alignment bars, depending in which one of the right and left sides of the patient the prosthesis is being implanted, perpendicular to a line which extends between the patient's right and left anterior/superior iliac spines perpendicular to the patient's pelvic line, inserting the oriented prosthesis in the acetabulum of he patient, and impacting the instrument for implanting the prosthesis in the acetabulum;

operating the instrument for disengaging the adapter from the implanted prosthesis;

unlocking the adapter from the instrument; and removing the unlocked adapter from the instrument.

5. A method as described by claim 4, wherein removably supporting the adapter on an instrument and locking the adapter thereon includes:

arranging the adapter and the instrument in sliding fit relation;

sliding the adapter on one end of the instrument;

providing a circumferential slot on the adapter;

supporting a locking arrangement on the instrument near the one end thereof and operating said locking arrangement for engaging the circumferential slot.

6. A method as described by claim 5, wherein removably engaging the prosthesis on an adapter includes:

engaging the prosthesis on the adapter in snap fit relation.

7. A method as described by claim 6, wherein operating the instrument for disengaging the adapter from the implanted prosthesis includes:
  operating the instrument to push against the implanted prosthesis for breaking the snap fit relation between said prosthesis and the adapter.

8. A method as described by claim 7, wherein unlocking the adapter from the instrument includes:
  operating the locking arrangement for disengaging the circumferential slot.

9. A method as described by claim 8, wherein removing the unlocked adapter from the instrument includes:
  sliding the unlocked adapter off of the instrument.

10. A method as described by claim 4, including:
  providing the adapter so that said adapter is disposable;
  using the adapter for a single implantation; and
  thereafter disposing of said adapter.

* * * * *